United States Patent [19]

Rydell

[11] Patent Number: 4,811,737
[45] Date of Patent: Mar. 14, 1989

[54] SELF-PURGING BALLOON CATHETER

[75] Inventor: Mark A. Rydell, Golden Valley, Minn.

[73] Assignee: Schneider-Shiley (USA) Inc., Minneapolis, Minn.

[21] Appl. No.: 120,658

[22] Filed: Nov. 16, 1987

[51] Int. Cl.$^4$ ............................................. A61M 29/02
[52] U.S. Cl. ...................................... 128/344; 604/96
[58] Field of Search ................... 128/344, 325, 348.1; 604/96–103, 104

[56] References Cited

U.S. PATENT DOCUMENTS

| | | | |
|---|---|---|---|
| 4,290,428 | 9/1981 | Durand et al. | 604/96 |
| 4,413,989 | 11/1983 | Schjeldahl et al. | 604/104 |
| 4,638,805 | 1/1987 | Powell | 128/344 |
| 4,693,243 | 9/1987 | Buras | 604/96 |
| 4,733,652 | 3/1988 | Kantrowitz et al. | 604/96 |
| 4,737,147 | 4/1988 | Ferrando et al. | 604/96 |

*Primary Examiner*—Max Hindenburg
*Attorney, Agent, or Firm*—Orrin M. Haugen; Thomas J. Nikolai; Frederick W. Niebuhr

[57] ABSTRACT

A tubular catheter having an inflatable expander member mounted thereon at the distal end thereof is provided with an extremely fine slit passing through the wall of the tubular catheter such that when a liquid is introduced under pressure into the proximal end thereof for inflating the balloon, any air present in the lumen of the catheter and in the yet unexpanded balloon is forced out through the slit. The slit or vent opening through the tube wall is so small that when the catheter is again aspirated to remove the purging fluid, air does not reenter the expander through the vent opening.

4 Claims, 1 Drawing Sheet

SELF-PURGING BALLOON CATHETER

BACKGROUND OF THE INVENTION

I. Field of the Invention

This invention relates generally to the manufacture and use of balloon tipped angioplasty catheters and more particularly to a means for facilitating the initial purging of air therefrom prior to their introduction into the vascular system of patients.

II. Discussion of the Prior Art

As an alternative to coronary bypass surgery, a procedure referred to as transluminal angioplasty has become increasingly popular because it is significantly less traumatic than the open-heart surgery required for a coronary bypass operation. As is explained in the Schjeldahl et al. U.S. Pat. No. 4,413,989, in carrying out transluminal angioplasty, an elongated flexible catheter having a balloon or expander member at its distal end is introduced at an appropriate location in the vascular system and then routed through the vascular system to the particular coronary artery, which has been found to be partially occluded by fatty deposits or other types of stenotic lesions. Once the catheter is in place and the expander member is properly positioned relative to the lesion, fluid, under relatively high pressure, is introduced into the lumen of the catheter and it flows into the expander member and inflates same so as to force open the occluded vessel.

In the initial stages of the surgery, upon removal of the balloon tipped catheter from its sterile package, it is necessary to purge the air from the catheter prior to its introduction into the patient. This is necessitated by the fact that, if air (a compressible fluid) is trapped in the catheter, the balloon cannot be inflated to an appropriate working pressure. Also, when inflated with a radiopaque marking liquid, the presence of air in the balloon may result in an error in the accurate positioning of the expander relative to the lesion being treated. Thus, it has been the practice to repeatedly fill and aspirate the catheter with a liquid, such as saline solution, in such a way such that the air in the catheter tends to be mixed and entrapped in the liquid and drawn out of the catheter.

Attempts have also been made to provide a small air passage in the balloon so that air can be forced out through it, but this has not been altogether successful because when the liquid is again aspirated and withdrawn from the balloon to cause the balloon to collapse and assume its low profile state prior to being introduced into the patient, air can again be drawn through that same tiny orifice and the purging step is effectively defeated. Other purging protocols have required that, following the inflation of the expander member and the elimination of air from the interior of the catheter and its distal balloon by inflation with saline, the balloon be dipped in a tray of sterile saline solution as the liquid is again aspirated from the catheter. The immersion of the balloon into the pan of saline solution prevents air from re-entering the catheter through the tiny port in the distally located balloon.

Cardiovascular surgeons have complained about the difficulty attendant in purging the catheter of its air prior to use. The aforementioned procedure is time consuming and requires additional equipment to be located in the operating room setting which is generally already somewhat crowded with surgical apparatus. Accordingly, it would be advantageous to provide a balloon tipped catheter for use in angioplasty procedures wherein the catheter can more conveniently be purged of air prior to its introduction into the patient's vascular system. It is accordingly a principal object of the present invention to provide such a catheter.

Another object of the invention is to provide an angioplasty catheter having an air pervious, liquid impervious unidirectional vent in the wall of the expander mounting tube which permits the egress of entrapped air during the purging operation but which becomes sealed and blocks the subsequent inflow of air as the purging liquid is aspirated from the catheter.

SUMMARY OF THE INVENTION

In accordance with the present invention, there is provided a balloon catheter of the type having an inflatable expander member at its distal end and a fine slit formed through the wall of the tube on which the balloon is affixed. More particularly, a slit approximately 0.010 inches long and of substantially zero width is cut through the wall of the expander mounting tube just proximal of the distal end seal between the expander and the expander mounting tube. Such a slit has been found to provide a sufficient opening to permit air to be purged through the fine slit and out the distal end of the mounting tube when a liquid is forced into the proximal end of the catheter at nominal working pressures for the catheter. After all of the air is forced out of the slit or orifice, the slit will become exposed to and wetted by the purging liquid. When a vacuum is again pulled on the catheter to draw out the purging liquid and to collapse the balloon against the periphery of the catheter body, the re-entry of any significant amount of air through that tiny slit is precluded. This is especially true if the guidewire has been inserted into the catheter, and the guidewire lumen has been purged with saline solution. This keeps fluid in contact with the vent eliminating re-entry of air.

DESCRIPTION OF THE DRAWINGS

The foregoing objects and advantages of the invention will become apparent to those skilled in the art from the following detailed description of a preferred embodiment when taken in conjunction with the accompanying drawings in which.

DETAILED DESCRIPTION OF THE PREFERRED EMBODIMENT

Figure 1:
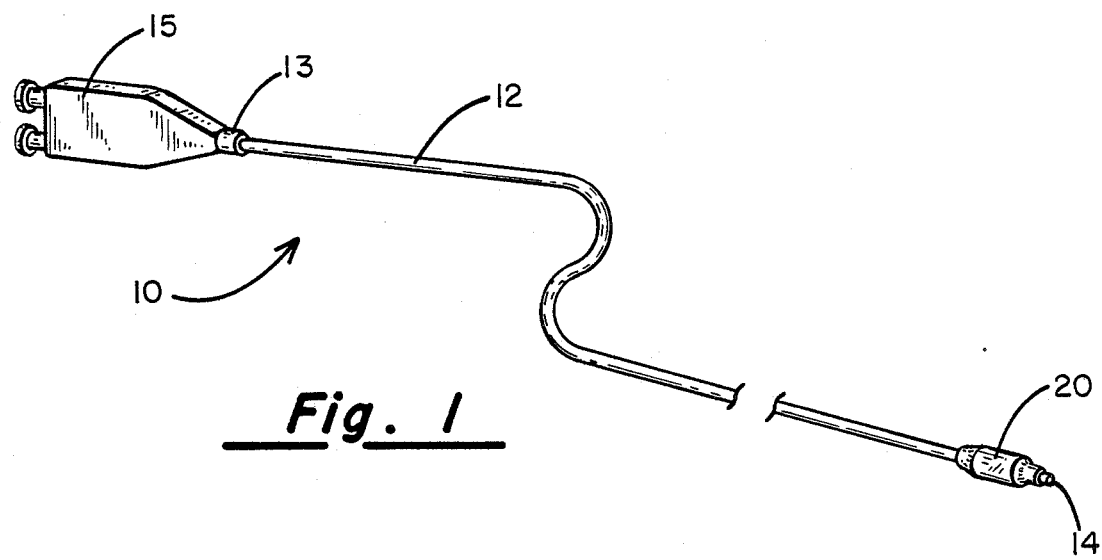
FIG. 1 is a perspective view of an angioplasty catheter.
Figure 2:
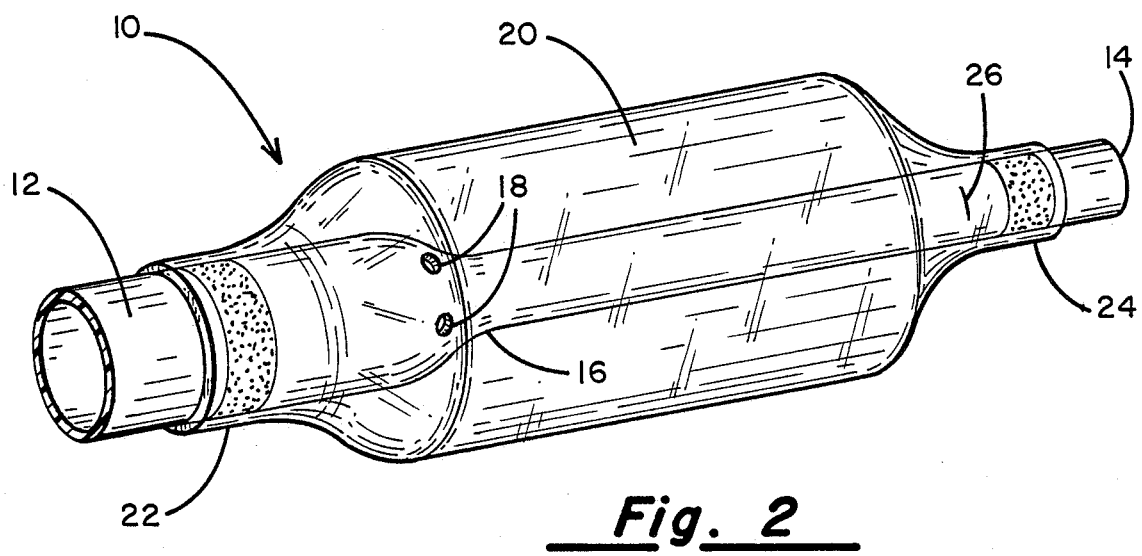
FIG. 2 illustrates by means of a greatly enlarged side view the distal end portion of the catheter of FIG. 1.

Referring to the drawings, in FIG. 2, there is shown a greatly enlarged side view of the distal end portion of the balloon-tipped catheter of FIG. 1, this catheter being of the type used in the conduct of coronary angioplasty procedures and embodying the features of the present invention. The catheter is indicated generally by numeral 10 and is seen to include an elongated, flexible, plastic tubular member 12 having a proximal end 13 and a distal end 14. Affixed to the proximal end of the catheter in a conventional fashion is a plastic hub 15 including, typically, an inflation port equipped with a luer lock fitting to which a syringe may be connected.

Toward the distal end of the catheter, the outside diameter of the elongated plastic tubular member 12 constricts to a lesser diameter in a transition zone 16 such that the distal end 14 thereof is of generally a lesser diameter than the overall diameter of the major portion of the tubular element 12. Located in the neighborhood of the transition zone 16 and passing through the wall of the tube 12 are one or more inflation ports 18 through which a fluid introduced into the lumen of the catheter body 12 at its proximal end may pass.

Located near the distal end of the catheter assembly is an expander member 20 in the form of a short length of a suitable biaxially oriented plastic material, such as polyethylene terephthalate, which is commonly referred to by the acronym PET. As illustrated, the expander member is tubular in form and is bonded at its proximal end 22 to the outer surface of the tubular member 12 while its distal end is sealingly bonded to the outer periphery of the reduced diameter portion at 24. Cut through the wall of the tubular member 12 just proximal of the distal end seal at 24 is a small, radially extending slit 26 which may typically be about 0.010 inches in length but of a width which is substantially closed, given the flexible, resilient nature of the plastic from which the tube 12 is formed.

When it is desired to purge air from the catheter, a liquid, such as sterile saline or a saline solution embodying a radiopaque material, may be injected by means of a syringe coupled to the luer fitting of the proximal hub 15 and that purging liquid will flow through the lumen 13 of the catheter forcing air ahead of it and ultimately through the inflation ports 18 to expand the "balloon" 20. With a suitable hydraulic pressure in excess of 100 psi applied, the entrapped air will escape out the slit 26. The purging liquid, being more viscous than air, cannot escape through the minute opening created by slit 26. By positioning the slit 26 just slightly inward of the seal 24, practically all of the air previously trapped within the catheter assembly will be exhausted and the inflation fluid will substantially fill the lumen of the tube 12 and expander 20.

Now, after all of the air has been purged from the catheter body and the expander member and it is desired to insert the catheter into the patient's vascular system, a suitable suction or source of negative pressure is coupled to the proximal end of the catheter through the fitting or hub 15 and the inflation liquid is evacuated from the catheter body, causing the expander member 20 to collapse and wrap itself closely about the outer profile of the catheter 12 in the zone thereof where the diameter is reduced. Because the slit 26 has been exposed to the inflation liquid, it is found that essentially no air can re-enter the expander 20 through the slit 26 from the outside. This is the case even tough the distal end portion of the catheter assembly need not be immersed in a tray of saline solution.

It is also recognized that persons skilled in the art might make changes and modifications to the embodiment described herein such as in the configurations of the catheter body itself. Rather than utilizing a single tubular member such as tube 12, two coaxial tubular members may be used where the expander member is joined at its proximal end to the outer tubular member and at its distal end to the outer periphery of the inner tubular member. In this configuration, the inflation fluid is made to flow through the space between the coaxially disposed tubes and the slit 26 will be formed through the side wall of the inner tubular member just proximal of the seal between it and the expander member 20.

The slit 26 is preferably formed in the radial or transverse direction as illustrated in FIG. 2 using a finely honed cutting instrument, such as a razor knife. When a small longitudinally extending slit was tried, it was found that the pressure build-up within the balloon and acting on the tube 12, typically about 100 psi, tended to tightly close and seal the slit, preventing the venting of air therethrough. With a radial slit or the laser machined hole, however, this did not occur.

It is also contemplated that the venting port may take the form of a small diameter precision hole passing through the wall of tube 12 rather than the slit 26. For example, a hole having a diameter in the range from 0.0005 to 0.0015 inches may be created with a laser beam and is sufficiently large to permit air to be vented, but sufficiently small to preclude the outflow of liquid. The later insertion of a guidewire through the central lumen of the expander mounting tube occurring during the angioplasty procedure also aids in preventing inflow of air back into the catheter via the slit or hole 26. A film of liquid building up between the guidewire and the inside wall of the tube 12 serves to plug the slit as the purging liquid is aspirated out the proximal end of the catheter.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. An intravascular catheter for use in transluminal angioplasty procedures of the type including an elongated, flexible, plastic, tubular catheter body having a proximal end and a distal end, at least one relatively large diameter opening formed through the side wall of said plastic tubular catheter approximate said distal end thereof, an inflatable tubular expander member sealingly affixed at opposed, spaced-apart ends thereof, the end seals being located proximally and distally of said opening, the improvement comprising:

a vent opening extending through the wall of said tubular catheter at a location slightly proximal of said end seal which is distal of said large diameter opening for venting air from said expander member when a liquid, under pressure, is introduced into said proximal end of said tubular catheter, said vent opening being of a size to preclude liquid flow therethrough and also precluding the re-entry of air into said expander member when said liquid is subsequently aspirated from said expander member.

2. The intravascular catheter as in claim 1 wherein said vent opening is a slit cut through the wall of said tubular catheter in the radial direction.

3. The intravascular catheter as in claim 2 wherein said slit is about 0.010 inches long.

4. The intravascular catheter as in claim 1 wherein said vent opening is a hole having a diameter in the range of from 0.0005 to 0.0015 inches.

* * * * *